(12) United States Patent
Petrich

(10) Patent No.: US 7,910,375 B2
(45) Date of Patent: Mar. 22, 2011

(54) TEST SYSTEM FOR ANALYZING BODY FLUIDS

(75) Inventor: Wolfgang Petrich, Bad Schönborn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/704,351

(22) Filed: Feb. 11, 2010

(65) Prior Publication Data

US 2010/0144048 A1    Jun. 10, 2010

Related U.S. Application Data

(62) Division of application No. 11/468,049, filed on Aug. 29, 2006, now Pat. No. 7,708,948.

(30) Foreign Application Priority Data

Sep. 1, 2005 (EP) ..................................... 05018973

(51) Int. Cl.
*G01N 33/00* (2006.01)

(52) U.S. Cl. ............ 436/164; 436/165; 436/95; 422/66; 422/82.05

(58) Field of Classification Search .................. 422/66, 422/82.05; 356/39; 436/165, 164, 95
See application file for complete search history.

(56) References Cited

U.S. PATENT DOCUMENTS

| 4,510,383 A | 4/1985 | Ruppender |
| 6,362,890 B1 | 3/2002 | Petrich et al. |
| 2001/0038808 A1* | 11/2001 | Tajima ........................... 422/56 |
| 2005/0201897 A1* | 9/2005 | Zimmer et al. ............ 422/82.05 |

FOREIGN PATENT DOCUMENTS

| WO | WO 02/100274 A1 | 12/2002 |
| WO | WO 2004/047642 A1 | 6/2004 |
| WO | WO 2004/056269 A1 | 7/2004 |
| WO | WO 2005/032372 A1 | 4/2005 |
| WO | WO 2005/034740 A2 | 4/2005 |

* cited by examiner

*Primary Examiner* — Jill Warden
*Assistant Examiner* — Dwan A Gerido
(74) *Attorney, Agent, or Firm* — Bose McKinney & Evans LLP

(57) ABSTRACT

The invention relates to a test system for analyzing body fluids of the type comprising a test element tape carrying a plurality of test elements, a tape deflector for the test element tape for the selective application of body fluid, and a light source as well as a detector for optically analyzing test elements to which body fluid has been applied. The tape deflector has a rotatable optical element which acts as a deflection roller during transport of the test element tape. The optical element is positioned in the optical path between the light source and the detector.

18 Claims, 2 Drawing Sheets

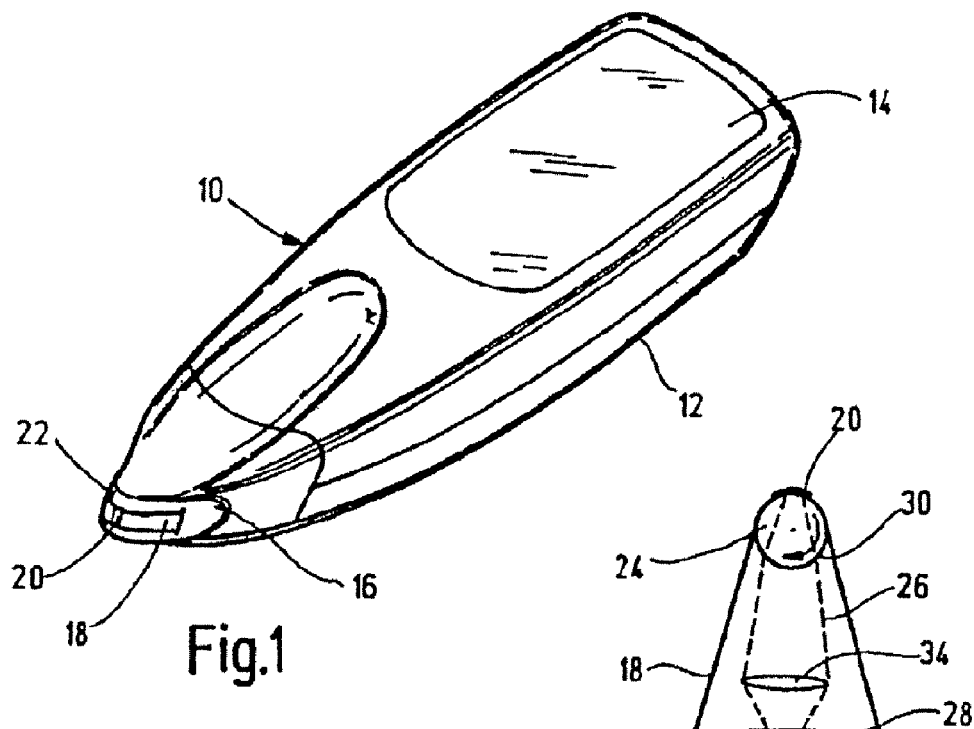
Fig.1
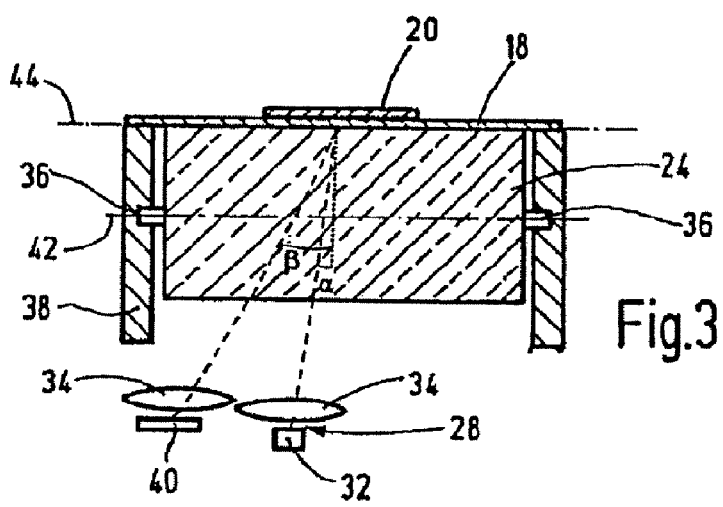
Fig.2
Fig.3
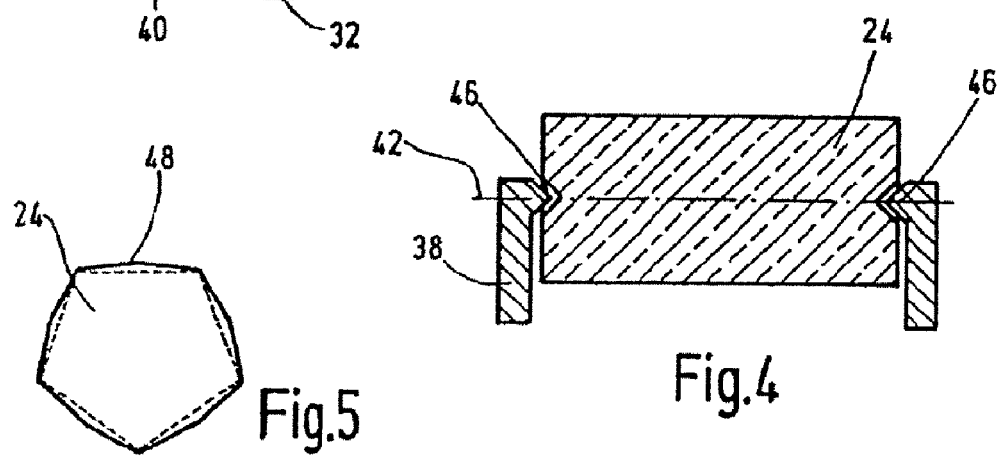
Fig.5
Fig.4

TEST SYSTEM FOR ANALYZING BODY FLUIDS

RELATED APPLICATIONS

This application is a divisional application of U.S. patent application Ser. No. 11/468,049 now U.S. Pat. No. 7,708,948 filed Aug. 29, 2006, which claims priority to EP 05 018 973, filed Sep. 1, 2005.

BACKGROUND

The present invention relates to a test system for analyzing body fluids, in particular blood, of the type comprising a test element tape carrying a plurality of test elements that is preferably wound in a tape cassette, a tape deflector for the test element tape for the directed application of body fluid, and a light source as well as a detector to optically analyze test elements to which body fluid has been applied.

Portable devices operating as minilaboratories, which can also be used by laymen to carry out the required steps in a simple and rapid manner are known for self-monitoring blood glucose by diabetics. In order to replace conventional test strips, it is proposed in WO 2004/047642 that instead of individual test strips, a wound test tape should be used on which a plurality of test fields provided with a suitable test chemistry are arranged consecutively. The body fluid is applied to a test field that is moved into an active position by advancing the tape over a tip and analyzed. Details on blood collection as well as on the known test media and detection systems especially for blood glucose are disclosed in this document to which reference is herewith made and the contents of which are incorporated by reference into this application. This document also shows that a transparent tip can be used to directly couple the instrument optics. Constraints that have to be observed in this case are that the total height of the deflector tip and its opening angle should be as small as possible but it should still be possible to optically analyze the test field for example on the basis of a reflectance measurement or a fluorescence measurement.

SUMMARY OF THE INVENTION

The present invention addresses the above-noted disadvantages and provides an improved and simplified system of the type mentioned above, and in particular, also reduces strain on the test tape in order to achieve a reliable measurement process in a compact instrument.

Exemplary embodiments of the present invention provide a deflector for the test tape which is advantageous for tape transport as well as for optical analysis. In exemplary embodiments, the tape deflector has a rotatable optical element positioned in or along the optical path between the light source and the detector. The optical element rotates to transport the test tape. The optical element, which rotates during tape transport, considerably reduces frictional losses in the tape deflection, thus considerably reducing the risk of tape deformation or of a tear in the tape. This also allows the use of thinner carrier tapes, which in turn, allows a greater quantity of tests to be provided within a given cassette volume. Moreover, the tape can be transported with less motor output and at the same time with less power consumption. The transparent optical element also creates a simple optical access to the test element without the test element having to be transported further to a distant measuring position.

The light permeable optical element preferably has a deflector surface that rests against the test element tape and can be rotated in the direction of tape transport to ensure a direct optical coupling in the measuring position and a rotation of the deflector as the tape advances.

Another advantageous embodiment provides that the optical element consists of a lens which focuses the light of the light source onto the respective test element to be analyzed on the test element tape. This allows imaging effects to be utilized for a miniaturization of the measuring field.

Another constructional improvement is achieved by designing the optical element as a cylindrical lens which is mounted so that it can rotate freely about its longitudinal axis and guides the test element tape on its outer surface.

For tape transport, it is favorable when the optical element has a circular, elliptical or polygonal rotationally symmetric cross-section.

The optical element can be rotatably mounted in a sleeve bearing, a pivot bearing or conical bearing to provide a simple bearing with sufficiently low friction.

Another advantageous embodiment of the optical coupling provides that the optical element in combination with a lens located downstream of the light source and/or upstream of the detector forms the imaging optics.

In order to screen the detector from ambient light, it is advantageous when a diaphragm is located in the area of an intermediate image between the test element tape and the detector.

According to a further exemplary embodiment, the detector is arranged outside of the area of incidence or of the optical axis of the light specularly (directly) reflected from the test element or of the light beam of the light source. In this manner it is possible to differentiate purely geometrically between the diffusely (in all directions) reflected light which provides the information on the analyte from the reagent layer of the test field, whereas the specular reflection does not reach the entry cross-section of the detector, at least not to a significant extent.

Such a geometric separation can be achieved by aligning the light source at an angle of incidence to the test element tape and aligning the detector at a larger detection angle in comparison thereto in a common plane on one side of the axis of incidence.

Another advantageous arrangement provides that the light source and the detector are arranged in a common half-space at a lateral distance from a boundary plane spanning the center line of the test element tape in the region of the tape deflector. The light that is reflected normally is essentially radiated into the other half-space without reaching the detector.

From a constructional point of view it is particularly advantageous when the light receiver and the detector are arranged on a support in an instrument which receives the tape cassette and are aligned with the tape deflector by means of an optical deflection means and in particular by a mirror integrated in the tape cassette.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein:

FIG. 1 is a perspective view of a blood sugar measuring instrument with a tape deflector for use of a test element tape;

FIG. 2 is a simplified cross-sectional view illustrating the tape deflector provided as a rotatable cylindrical lens in conjunction with a reflectometric measuring device;

FIG. 3 shows a longitudinal section through the arrangement of FIG. 2;

FIG. 4 shows another embodiment of an optical deflection roller in a view corresponding to FIG. 3;

FIG. 5 shows a polygonal deflection roller in profile;

Corresponding reference characters indicate corresponding parts throughout the several views.

DETAILED DESCRIPTION

Figure 6:
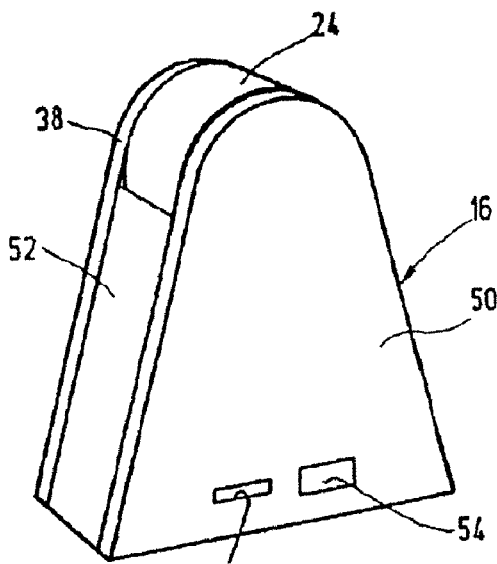
FIG. 6 is a perspective view of a cassette part containing the deflection roller for the test element tape.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

FIG. 1 shows a test system for body fluids and in particular a blood sugar measuring instrument 10 in the form of a portable hand-held instrument. It includes an instrument housing 12 with a display 14 in which a tape cassette 16 can be inserted as a consumable part. The cassette contains a test element tape 18 which is expediently provided with test elements or test elements 20 spaced apart on sections thereof. Body fluid (blood) can be applied to the test elements 20 in order to quantitatively detect an analyte (glucose) contained therein by means of a reflectometric measurement.

The individual test elements 20 are moved successively into a receiving position or testing position in the deflection area in which their front faces are accessible for a selected application of a small amount of body fluid by winding the test tape 18 forwards over a tape deflector 22 that has a basic V-shaped form. The optical measurement takes place from the rear side of the tape through the tape deflector 22 wherein the test element tape can have a transparent carrier foil or a tape cut-out in the area of the test elements 20. After measurement, the used test element 20 is wound onto a take-up spool of the tape cassette 16 during which an unused test field on the adjoining section of tape is drawn off from a supply spool. In this manner the user can carry out a plurality of tests in an automated measuring process without requiring complicated handling steps.

As shown in FIG. 2, the tape deflector 22 has a transparent rotatable lens element 24 positioned in the optical path 26 of the optical measuring device 28. The outer wall 30 of the circularly cylindrical lens element 24 composed of glass or transparent plastic forms a deflection surface which rotates with the test element tape 18 during tape transport so that only slight frictional losses occur. At the same time, the lens element 24 focuses the measuring light generated by the light source 32 of the measuring device 28 onto the test element 20 that is present at that time in the receiving position. In order to improve the light yield, a converging lens can be arranged in front of it.

FIG. 3 shows a possible sleeve bearing of the cylindrical lens 24 in the form of front-facing pivot bearings 36 in the side walls 38 of the cassette 16. FIG. 3 also shows a possible arrangement of the light source 32 and detector 40 of the measuring device 28 for the detection of the measuring light that is diffusely reflected from the test element 20. For this purpose, the detector 40 is arranged outside of the optical axis of the light from the light source 32 that is specularly reflected from the facing rearside of the test element 20. In the embodiment illustrated in FIG. 3, the light source 32 and the detector 40 are aligned in one plane which extends through the axis of rotation 42 of the cylindrical lens 24 and the zenithal line 44 of the tape deflector wherein the detector 40 is arranged at a larger receiving angle β compared to the beaming angle α of the light source 32.

FIG. 4 shows another alternative for the simple pivoting of the cylindrical lens 24. In this example front-facing conical bearings 46 are provided for a low friction point contact. A low positioning tolerance is employed, especially perpendicular to the axis of rotation 42, as well as low friction and ability to be manufactured economically.

As shown in FIG. 5, the lens or deflection roller 24 can also have a polygonal geometry instead of a circular cross-section. In the embodiment shown, the basic shape is that of a pentagon in order to thus achieve better defined transport paths for the tape transport. In this case, the side surfaces 48 are rounded or chamfered in order to advantageously design the optical paths.

According to FIG. 6, the tape cassette 16 can have a cassette tip 50 with V-shaped converging tape guide surfaces 52 where the cylindrical lens 24 is positioned in the apex region. Form-locking structures (not shown) can be provided within the cassette tip 50 for exact alignment when the measuring device 28 is attached where openings in the walls 54, 56 allow the light source and detector to be engaged from below.

Figure 7:
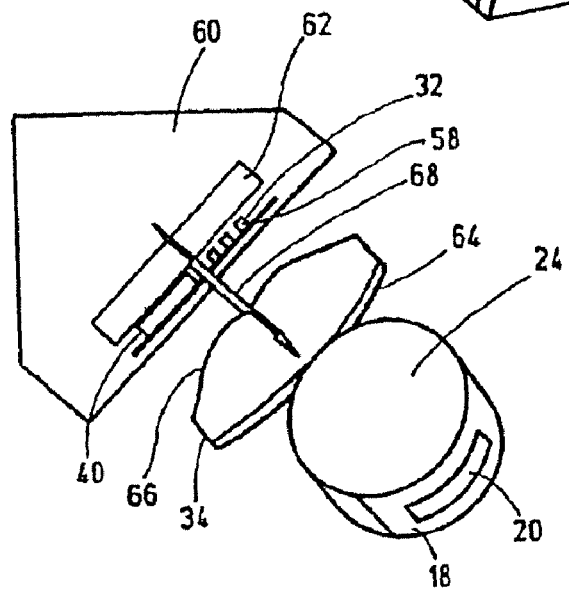
FIG. 7 is a sectional perspective view showing a measuring arrangement of the blood sugar measuring instrument.
Figure 8:
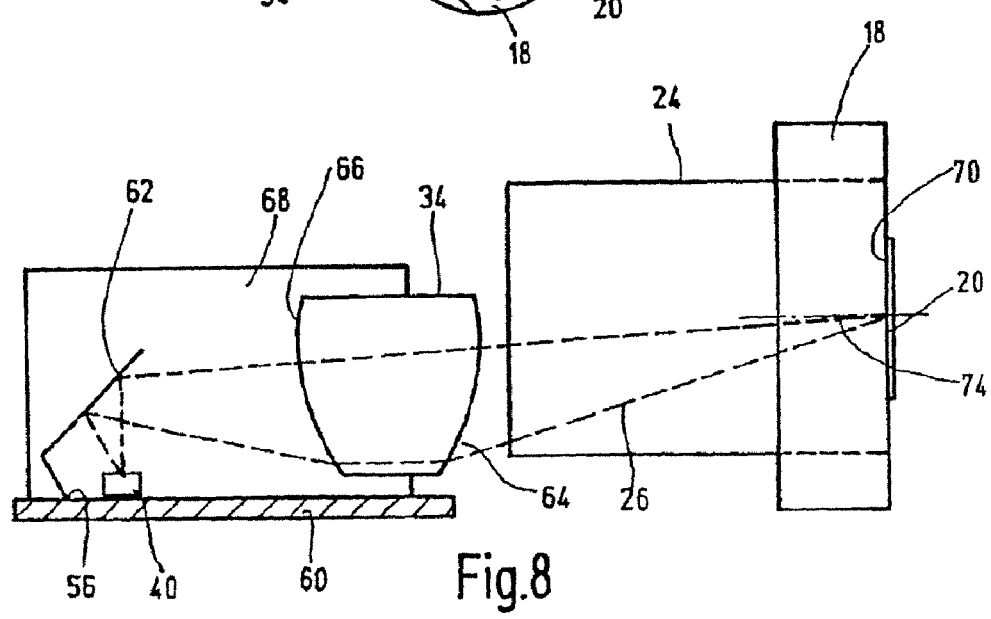
FIG. 8 shows a partial sectional side-view of the arrangement of FIG. 7.

As shown in FIGS. 7 and 8, the light source 32—in the form of three LEDs 58—and the detector 40 are arranged on an instrument mainboard 60, whereas the optical light path is determined by elements on the cassette. In detail, these elements are a deflecting mirror 62, a converging lens 34 and the cylindrical lens 24 as a deflection roller for the test tape 18. The lens 34 arranged in front has a simple convex lens surface 64 facing the deflection roller and a double convex lens surface 66 facing the measuring device 28 where a central diaphragm 68 between the lens segments separates the light source 32 from the detector 40.

Also in this case the geometric arrangement of the optical elements ensures that only light that is diffusely reflected from the rear side 70 of the test element 20 is detected. For this purpose the light source 32 and the detector 40 are arranged in the half-space below the plane extending through the centre line 74 of the test tape such that the specularly reflected light is essentially radiated into the half-space above it. Calculations made on this configuration show that the proportion of specularly reflected light detected in the detector relative to the total emitted light of the light source is less than 0.001 ppm whereas the ratio of detected to emitted light is about 0.13%. Hence, this ensures that mainly only diffusely reflected light from the reagent layer of the test element 20 is detected.

In summary, it may be ascertained that the embodiments disclosed herein concern a test system for analyzing body fluids and in particular blood comprising a test element tape 18 carrying a plurality of test elements 20, a tape deflector 22 for the test element tape for the selective application of body fluid and a light source 32 as well as a detector 40 for optically analyzing test elements to which body fluid has been applied. The tape deflector 22 has a rotatable optical element 24 as a deflection roller to transport the test element tape 18 in the optical path between the light source 32 and detector 40.

While exemplary embodiments incorporating the principles of the present invention have been disclosed herein-above, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS

10 Blood sugar measuring instrument
12 Instrument housing
14 Display
16 Tape cassette
18 Test element tape
20 Test element
22 Tape deflector
24 Lens element
26 Optical path
28 Optical measuring device
30 Outer wall
32 Light source
34 Converging lens
36 Front-facing pivot bearing
38 Side wall
40 Detector
42 Axis of rotation
44 Zenithal line
46 Front-facing conical bearing
48 Side surface
50 Cassette tip
52 Tape guide surface
54 Opening in the wall
56 Opening in the wall
58 LED
60 Instrument mainboard
62 Deflecting mirror
64 Convex lens surface
66 Double convex lens surface
68 Central diaphragm
70 Rear side
74 Centre line

What is claimed is:

1. A method of using a test system having a test element tape for analyzing body fluids, comprising:
   positioning an optical element adjacent the test element tape;
   advancing a test element of the test element tape to a testing position while rotating the optical element;
   projecting light through the optical element and onto the test element; and
   detecting light that is reflected from the test element and that passes through the optical element.

2. The method of claim 1, further comprising the steps of:
   applying a body fluid sample to the test element prior to the projecting step; and
   analyzing the detected light for presence or concentration of an analyte in the body fluid sample.

3. The method of claim 2, wherein the analyte is glucose.

4. The method of claim 1, wherein the optical element is cylindrical.

5. The method of claim 1, further comprising frictionally engaging the optical element with the test tape while advancing the test element.

6. The method of claim 1, further comprising passing one of the projected and the detected light through a second optical element.

7. The method of claim 1, wherein the step of positioning the optical element comprises positioning the optical element adjacent and in contact with the test element tape.

8. The method of claim 1, wherein the step of projecting light comprises using a light source to project light through the optical element.

9. The method of claim 1, wherein the test element is advanced by the rotating of the optical element.

10. A method of using a test system having a test element tape for analyzing body fluids, comprising:
    positioning an optical element adjacent and in contact with the test element tape;
    advancing a test element of the test element tape to a testing position while rotating the optical element;
    projecting light through the optical element and onto the test element; and
    detecting light that is reflected from the test element and that passes through the optical element.

11. The method of claim 10, further comprising the steps of:
    applying a body fluid sample to the test element prior to the projecting step; and
    analyzing the detected light for presence or concentration of an analyte in the body fluid sample.

12. The method of claim 11, wherein the analyte is glucose.

13. The method of claim 10, wherein the optical element is cylindrical.

14. The method of claim 10, further comprising frictionally engaging the optical element with the test tape while advancing the test element.

15. The method of claim 10, further comprising passing one of the projected and the detected light through a second optical element.

16. The method of claim 10, wherein the step of positioning the optical element comprises positioning the optical element adjacent and in contact with a test element.

17. The method of claim 10, wherein the step of projecting light comprises using a light source to project light through the optical element.

18. The method of claim 10, wherein the test element is advanced by the rotating of the optical element.

* * * * *